(12) United States Patent
Hannula et al.

(10) Patent No.: US 12,303,297 B2
(45) Date of Patent: May 20, 2025

(54) METHOD AND ARRANGEMENT TO HELP A MOTHER WITH HER BABY TO FIND OPTIMAL LIFE AND CARE RHYTHM

(71) Applicant: NUCU OY, Oulu (FI)

(72) Inventors: Juha Hannula, Kiiminki (FI); Esko Alasaarela, Oulu (FI)

(73) Assignee: NUCU OY, Oulu (FI)

( * ) Notice: Subject to any disclaimer, the term of this patent is extended or adjusted under 35 U.S.C. 154(b) by 910 days.

(21) Appl. No.: 17/593,731

(22) PCT Filed: Mar. 23, 2020

(86) PCT No.: PCT/FI2020/000005
§ 371 (c)(1),
(2) Date: Sep. 23, 2021

(87) PCT Pub. No.: WO2020/193842
PCT Pub. Date: Oct. 1, 2020

(65) Prior Publication Data
US 2022/0167930 A1  Jun. 2, 2022

(30) Foreign Application Priority Data
Mar. 26, 2019  (FI) ........................................ 20195231

(51) Int. Cl.
*A61B 5/00* (2006.01)
*A61B 5/01* (2006.01)
(Continued)

(52) U.S. Cl.
CPC .............. *A61B 5/7267* (2013.01); *A61B 5/01* (2013.01); *A61B 5/024* (2013.01); *A61B 5/05* (2013.01);
(Continued)

(58) Field of Classification Search
CPC ......... A61B 5/7267; A61B 5/01; A61B 5/024; A61B 5/05; A61B 5/08; A61B 5/1118;
(Continued)

(56) References Cited

U.S. PATENT DOCUMENTS 3,809,065 A * 5/1974 Gatts ...................... A61G 11/00
600/27
4,066,072 A * 1/1978 Cummins ............ A47C 27/085
601/161
(Continued)

FOREIGN PATENT DOCUMENTS

EP  2 659 929 A2  11/2013
GB  2 331 887 A  6/1999
(Continued)

OTHER PUBLICATIONS

Finnish Search Report dated Oct. 24, 2019 for Finnish Application No. 20195231.
(Continued)

*Primary Examiner* — Sunita Reddy
(74) *Attorney, Agent, or Firm* — Ziegler IP Law Group, LLC.

(57) ABSTRACT

An intelligent baby caring method and arrangement helps to recognize and maintain emotional interaction between mother and her baby and to improve the baby's life rhythm and calm and soothe him/her automatically when needed and help him/her to fall asleep and to wake up at the most convenient time and way. The aim is to help the mother with her baby to find optimal life and care rhythm. The invention is focused on a platform (101) with many sensors, sensor sheet (120), a transducer to produce acoustic and mechanical vibrations (14) and an airflow blower (132). Sensors are also fixed to the mother (10) and in the care room (198). A sleep/activity graph of the baby and sleep/emotion graph of the mother are measured and tracked with multimodal (Continued)

sensors and an artificial intelligence unit (200) processes audio, motion and airflow actions given to the baby from the platform to help the baby to move from an improper to optimal sleep/activity level.

20 Claims, 6 Drawing Sheets

(51) Int. Cl.
| | |
|---|---|
| A61B 5/024 | (2006.01) |
| A61B 5/05 | (2021.01) |
| A61B 5/08 | (2006.01) |
| A61B 5/11 | (2006.01) |
| A61B 5/16 | (2006.01) |
| A61B 5/20 | (2006.01) |
| A61F 7/00 | (2006.01) |
| A61H 23/02 | (2006.01) |
| A61M 16/00 | (2006.01) |
| A61M 21/00 | (2006.01) |

(52) U.S. Cl.
CPC ............. *A61B 5/08* (2013.01); *A61B 5/1118* (2013.01); *A61B 5/16* (2013.01); *A61B 5/20* (2013.01); *A61B 5/4094* (2013.01); *A61B 5/42* (2013.01); *A61B 5/4812* (2013.01); *A61B 5/4818* (2013.01); *A61B 5/746* (2013.01); *A61F 7/0053* (2013.01); *A61B 2503/045* (2013.01); *A61H 23/02* (2013.01); *A61H 2201/0146* (2013.01); *A61H 2201/0207* (2013.01); *A61H 2201/0214* (2013.01); *A61H 2201/5007* (2013.01); *A61H 2230/00* (2013.01); *A61M 16/0066* (2013.01); *A61M 2021/0016* (2013.01); *A61M 2021/0022* (2013.01)

(58) Field of Classification Search
CPC ........... A61B 5/16; A61B 5/20; A61B 5/4094; A61B 5/42; A61B 5/4812; A61B 5/4818; A61B 5/746; A61B 2503/045; A61F 7/0053; A61H 23/02; A61H 2201/0146; A61H 2201/0207; A61H 2201/0214; A61H 2201/5007; A61H 2230/00; A61H 1/00; A61M 16/0066; A61M 2021/0016; A61M 2021/0022; A61M 2021/0027; A61M 2021/0061; A61M 2021/0066; A61M 2021/0083; A61M 2021/0088; A61M 2205/07; A61M 2205/18; A61M 2205/3303; A61M 2205/3306; A61M 2205/3317; A61M 2205/3368; A61M 2205/3375; A61M 2205/3569; A61M 2205/3593; A61M 2205/505; A61M 2205/582; A61M 2205/82; A61M 2210/04; A61M 2210/145; A61M 2230/04; A61M 2203/06; A61M 2230/10; A61M 2230/205; A61M 2230/40; A61M 2230/42; A61M 2230/50; A61M 2230/60; A61M 2230/62; A61M 2230/63; A61M 2230/65; A61M 2240/00; A61M 21/02; A61M 2205/332; A61M 2205/52; G16H 20/30; G16H 40/63; G16H 40/67; G16H 50/20; G16H 50/30; G16H 20/70; G06N 5/01; G06N 20/00; G06N 3/08

USPC ...................................................... 600/26–28
See application file for complete search history.

(56) References Cited

U.S. PATENT DOCUMENTS

| | | | | |
|---|---|---|---|---|
| 4,694,839 | A * | 9/1987 | Timme | A61H 23/0263 600/534 |
| 5,205,811 | A * | 4/1993 | Fornarelli | A47G 9/1045 600/28 |
| 10,201,236 | B1 * | 2/2019 | Cloud | A47G 9/1045 |
| 2007/0179334 | A1 * | 8/2007 | Groves | A61M 21/00 600/26 |
| 2008/0020672 | A1 * | 1/2008 | Osborn | A63H 33/006 446/227 |
| 2008/0178384 | A1 * | 7/2008 | Lord | A47D 15/008 5/93.1 |
| 2010/0125949 | A1 | 5/2010 | Stebbing | |
| 2013/0096368 | A1 * | 4/2013 | Devroey | A61B 5/112 29/896.2 |
| 2014/0330070 | A1 | 11/2014 | Anabalón Alamos et al. | |
| 2015/0105608 | A1 | 4/2015 | Lipoma et al. | |
| 2015/0126803 | A1 | 5/2015 | Rapoport | |
| 2015/0201846 | A1 * | 7/2015 | Maiershon | G16H 40/67 600/301 |
| 2015/0250978 | A1 * | 9/2015 | Pelsue | A61M 21/02 600/28 |
| 2015/0273698 | A1 * | 10/2015 | Bender | B25J 11/009 901/1 |
| 2016/0035205 | A1 | 2/2016 | Messenger et al. | |
| 2016/0174728 | A1 | 6/2016 | Karp et al. | |
| 2016/0293042 | A1 * | 10/2016 | Pradeep | A61B 5/002 |
| 2016/0345832 | A1 | 12/2016 | Pavagada et al. | |
| 2017/0043118 | A1 | 2/2017 | Karp et al. | |
| 2017/0072162 | A1 * | 3/2017 | Kim | A61M 21/02 |
| 2017/0340285 | A1 | 11/2017 | Rubin et al. | |
| 2019/0046072 | A1 * | 2/2019 | Sham | A61B 7/00 |
| 2019/0083003 | A1 | 3/2019 | Lee et al. | |
| 2019/0130720 | A1 * | 5/2019 | Lui | G06V 10/82 |
| 2021/0212477 | A1 * | 7/2021 | James | A47D 9/057 |

FOREIGN PATENT DOCUMENTS

| | | |
|---|---|---|
| JP | 2010-210730 A | 9/2010 |
| WO | WO 2011/063077 | 5/2011 |
| WO | WO 2018/039433 | 3/2018 |
| WO | WO 2018/075566 | 4/2018 |

OTHER PUBLICATIONS

Ferdinando, Henry, "Comparing Features from ECG Pattern and HRV Analysis for Emotion Recognition System", Conference Papers 2016.
Janney, Bethanny et al., "Design of Mobile Infant Incubator with Comforting Pillow" Article 2018.
Nandhini et al., "Design of an Intelligent Pillow with Maternal Temperature and Heartbeat Vibrations for Comforting NICU Infants", Article—Indian Journal of Science and Technology, Sep. 2016.
Ranta, Jukka, Sleep Classification in Infants, Using a Bed Mattress Sensor and Analysis of ECG, Aalto University, May 2018.
Wozniak, Piotr, Good Sleep, Good Learning, Good Life, SuperMemo Articles, Sep. 2021.
International Search Report for PCT/FI2020/000005 dated Jun. 22, 2020, 6 pages.
Written Opinion of the ISA for PCT/FI2020/000005 dated Jun. 22, 2020, 9 pages.
Extended European Search Report issued on Nov. 9, 2022 in corresponding European Application No. 20779216, 14 pages.

* cited by examiner

METHOD AND ARRANGEMENT TO HELP A MOTHER WITH HER BABY TO FIND OPTIMAL LIFE AND CARE RHYTHM

This application is the U.S. national phase of International Application No. PCT/FI2020/00005 filed Mar. 23, 2021 which designated the U.S. and claims priority to FI Patent Application No. 20195231 filed Mar. 26, 2019, the entire contents of each of which are hereby incorporated by reference.

The aspects of the disclosed embodiments generally relate to baby care problems, and more particularly, to a device, system and method for helping after birth to recognize and maintain emotional interaction between mother and her baby and to improve the baby's life rhythm and calm and soothe him/her automatically when needed and help him/her to fall asleep and to wake up at the most convenient time and way.

BACKGROUND

Any baby has heard and sensed his/her mother's many sounds, motions and warmness, including heart and respiratory pulses and fluctuations, during the nine months in the uterus. Also, the mother has felt the fetus' movements and recognized its life rhythm. In addition, biochemical and hormonal changes have effects in both directions. Therefore, emotional and even psycho-somatic interaction could be said to have been present when the baby has been as a fetus in the uterus. The change from the intrauterine environment to the extra-uterine environment at birth is one of the most difficult transitions for a mammal in its lifetime. A very different new way to live begins at birth and, for example, a periodical rhythmic sleeping routine must be learned.

Within the first three months babies sleep 14-17 hours per day in many periods. During sleeping the baby stays in different sleep levels, which are called REM, NREM1, NREM2, NREM3 and NREM4, from lightest REM (REM=Rapid Eye Movement) to the deepest one NREM4 (NREM=Non-Rapid Eye Movement). While being awake the baby also stays in different activity levels, which are here called Drowsy, Vital, Morose and Panic. Sleep and activity levels can be measured with different sensors and by audio-visual evaluation.

Babies, especially premature babies, may suffer postnatal stress from detachment from the intrauterine environment. This may result in the baby gaining less restfulness and less sleep than is desirable, and further it may cause endless crying by the newborn and even long-term effects in personality of the child. The sleep disorders caused by a postnatal stress disorder may continue and affect still during adulthood, and similarly calming and sleep inducing help may be desirable for adults, too. One more babies' sleeping problem is so called SIDS seizure (Sudden Infant Death Syndrome), when a baby without any previous symptoms stops breathing and dies. The baby can be rescued by just waking him/her up by shaking.

Many techniques, methods and devices have been proposed and developed for calming babies in order to put them to sleep. It has been always known by parents that motion, sound and touch, for example lulling and lullabies, may help babies to calm down from Panic to Drowsy level and to fall asleep first to REM level. Thus, various sleep inducer and baby calmer devices using motion and sound have been proposed and developed. Further, to help a newborn to adapt for the transition from the intrauterine environment to the extra-uterine environment and to reduce possible stress of a newborn, various uterine motion and sound stimulation devices and methods have been proposed. Such devices aim to produce a sound characteristic of the uterus, like intrauterine cardiovascular and gastro-intestinal sounds. Particularly, the mother's heartbeat sound, which the baby came to know during gestation, is known to be important for calming and soothing effect.

A research paper by Chen et al. "Mimo Pillow—An Intelligent Cushion Designed with Maternal Heart Beat Vibrations for Comforting Newborn Infants", in IEEE Journal of Biomedical and Health Informatics, vol. 19, no 3, pages 979-985, proposes a method to comfort a baby by creating feeling of his/her mother's presence and care. They write: "Mimo aims at providing a comforting solution with qualities similar to those of being held to a parent's chest, available especially when the parent cannot provide the comfort him- or herself. This concept might not only increase the general comfort level, but it can also contribute to the bonding between parent and infant. Mimo gives parents the chance to record their personal features such as heartbeat, smell and temperature, which can be mediated to the child when it is in need of comfort. When the concept is fully realized, the child might experience a feeling as the parents were close to them, even when the parents are not physically there." Practically, they have done a simple prototype for recording the mother's heartbeat from fingertip by using photoplethysmography (PPG) sensor and repeating the heart-pulse vibrations from a pillow to the baby's head. A study of ten preborn babies shows that it helps to calm a crying baby significantly faster from a diaper change than without vibrations.

Another similar study is described by Nandhini et al. "Design of an Intelligent Pillow with Maternal Temperature and Heartbeat Vibrations for Comforting NICU Infants" in Indian Journal of Science and Technology, Vol 9 (33), September 2016. They measure and supply the mother's body temperature in addition to her heart-beat vibrations.

One more cushion type baby calming prototype is described by Bethanney Janney et al. "Design of Mobile Infant Incubator with Comforting Pillow", in International Journal of Engineering & Technology, 7 (2.25) (2018) 6-9. They control air humidity in addition to temperature and heart-beat vibrations of the mother.

Reviewing of the prior art reveals some US and other patents considering this matter. U.S. Pat. No. 3,672,354 discloses a device having an inflatable cushion comprising of an air compressor, which generates pressure pulses at the frequency of the human heartbeat.

U.S. Pat. No. 4,079,728 discloses an baby environment transition system, which simulates temperature, light, tactile sensation, motion and sounds sensed by the baby in the near gravid uterus and gradually permits the change of these simulative parameters.

U.S. Pat. No. 5,063,912 discloses a baby sleep-inducer and baby calmer device including a self-contained energy source, a self-contained sound developer and protective casing means, and producing a sound characteristic of a uterus sound to provide soothing, calming and sleep-inducing effect for a newborn.

U.S. Pat. No. 5,865,771 describes a mat which is intended to be used inside an incubator and which includes embedded electromechanical vibration transducers converting intra-uterine sounds, music, and the like into comfortable coenesthetic acoustic vibrations.

U.S. Pat. No. 6,004,259 discloses a sound activated device that enables the mother to record her own heartbeat on a memory device and in turn the played back sound is activated by crying of her baby, which serves as a calmer and soother sound to sleep.

JP 5278952 discloses a diagnostic device of babies' feelings and a method to perform diagnosis of feeling by analyzing interaction between babies' feeling and mother's feeling. In the depicted environment (for example, at home) a microphone is attached to a baby and a bone conduction microphone is attached to the mother. By attaching the bone-conduction microphone to the mother, it is possible to reduce noise when inputting the mother's voice to the depicted system.

US 2004/0077287 depicts a parent-infant attachment comprising a pouch for a baby. The depicted pouch system includes means for producing simulated parental body temperature, means for producing simulated parental heartbeat, means for producing simulated parental voice and means for producing simulated parental breathing. By the depicted device it is possible to perform adequate "Kangaroo Care" parent-infant attachment in the absence of biological parents.

WO 2011/063077 A1 depicts a device for simulation of noise and motion in a uterus, recorded from the mother and reproduced by speakers.

GB 2331887 A describes an audio device to create a comfortable environment for a baby by recording, for example, the heartbeat of the mother and reproducing the heartbeat with loudspeakers in a mattress.

EP2659929B1 discloses a sensory and stimulating system and device to create real-time sensory stimuli, corresponding to the outgoing of a caregiver sensory stimuli.

WO2018075566A1 discloses devices and methods to detect and analyze baby's crying by microphones and induce sounds and platform movements for automatically calming the crying baby.

US20150045608A1 describes an Infant calming/sleep-aid, SIDS prevention device, and method of use, with a moving platform that moves in a variable manner with accompanying variable sound generation, the sound and motion adapted to calm a fussy baby, induce sleep, and maintain sleep under normal conditions.

US 2019083003 A1 describes an infant care system for a caregiver to monitor and manage sleep metrics, patterns and quality. It is based on sensors, a communication device and a remote server, which gives recommendations of actions according to measured sensor data and information given by the caregiver in a couple of queries.

An article of Dr Piotr Wozniak published in May 2012 in SuperMemo webservice (https://www.supermemo.com/en/articles/sleep) "Good sleep, good learning, good life" gives a good knowledge about human sleeping rhythms, which play an important role in the aspects of the disclosed embodiments.

One interesting new technology for manufacturing sensors for baby care devices is printable electronics. In future it will be possible to print sensors, for example on baby sheets or baby clothing.

Prior art baby calming and sleep inducing devices suffer from significant disadvantages, because current methods and devices do not utilize or support babies' natural sleeping rhythms and the many factors affecting to falling asleep and to waking up from sleep or wake up from SIDS seizure. Thus, among other benefits, the babies' individual properties are not used in selecting the ways to calm the baby in sleep or wake him/her up and the means to predict the sleeping periods are not utilized. In addition, there are still many problems in quality of emotional interaction between the mother and her baby and in usability, practicality and manufacturability of the devices.

Thus, there is a need for an improved baby caring, calming and sleep-inducing device that indicates and utilizes baby's rhythms of sleep/activity levels and provides uterus environment sounds and motion sensation as well as feeling of the own mother's care, which matches better to emotional conditions of the baby and her mother, has adaptive and smart functionality, is easy and practical to use, and has a thin and practical design.

SUMMARY

The aspects of the disclosed embodiments tend to solve a problem of improper sleep/awake rhythm and wider thinking defective sleep/activity rhythm and habits, which are caused by big physiological and mental change and weakened interaction between mother and her baby, which have arisen from coming out of the uterus. The solution is based on automatic production of audio, motion and airflow actions resulted by an artificial intelligence system after processing of multisensory data measured from both the baby and the caregiver.

In the disclosed embodiment different variables are measured, processed and tracked from the baby by utilizing multimodal sensors and data processing system. Movement sensors, like accelerometers, are used to measure motion of the baby's hands, legs, head and body. Microphones are used to listen, record and track the baby's crying, joggling, talking, breathing, excreting, farting, burping and silence. Chemical sensors are used to measure and record sweating, urinating, excreting, puking and other activities with chemical contaminants. Biosensors are used to measure and track, for example, the baby's body temperature (daily variations, not only fever) heart activities (pulse, ECG), lung activities (breathing rate and airflow curve, pauses, sighs etc.), blood circulation (oxygen saturation, flow volume, blocks, body temperature distribution etc.), brain activities (EEG, oxygen saturation etc.), muscle activities (EMG), skin activities (conductance, sweating, temperature etc.) and gastro/metabolic activities.

According to the disclosed embodiments the sensors and data processing system are used to measure, save and track sleep/activity levels of the baby as a function of time. The sleep/activity levels can be categorized, for example, in five well-known sleep levels (REM, NREM1, NREM2, NREM3 and NREM4) and four awaken levels: Drowsy, Active, Morose and Panic. Categorizing is based on, for example, continuous artificial neural network (ANN) process of several sensor signals. Main categorizing algorithms are based on well-known research knowledge of human sleeping (See, for example, J. Ranta, Sleep classification in infants using a bed mattress sensor and analysis of ECG. Master's Thesis. Aalto University, 2018)

In addition, a learning part of categorizing is based on continuous adjusting of the neural computing parameters according to the tracking history of several sensor signals, individually for each baby. Both short term (minutes or even hours) and long term (days, months and even years) tracking history is useful in the learning algorithms. Tracking of baby's sleep/activity level results in the baby's sleep/activity graph as a function of time.

In addition, according to the aspects of the disclosed embodiments, emotional status and sleep levels of the mother (mother means later in this text also any other baby caregiver) is measured, saved and tracked by using similar sensors and a data processing system. These sensors can comprise, for example, acceleration and gyro sensors to track the mother's body and arms movements, microphones to listen e.g. to the mothers speaking, humming, singing, breathing, sighing, and in addition the environmental sounds coming from the home life, other children, kitchen machinery and outdoor traffic, and biosensors to measure and track the mother's body temperature (fever and daily variations of the body temperature) heart activities (pulse, ECG etc.), lung activities (breathing rate and airflow curve, pauses, sighs etc.), blood circulation (oxygen saturation, flow volume, blocks, body temperature distribution etc.), brain activities (EEG, oxygen saturation etc.), muscle activities (EMG), skin activities (conductance, sweating etc.) and gastro/metabolic activities. The mother's sensor unit comprises advantageously also an alarming actor, e.g. vibration device, to give soft and friendly alarms from the system.

Categorizing of the mother's emotional status is based on, for example, continuous neural network processing of several sensor signals. The emotional categories can be, for example, Peaceful, Joyful, Frustrated and Angry, as is presented in this description, but many other emotional categories and their combinations can alternatively be used in the aspects of the disclosed embodiments. Main categorizing algorithms are based on well-known research knowledge of human emotions. (See, for example, the next paper and its references: H. Ferdinando, T. Seppanen & E. Alasaarela, Comparing Features from ECG Pattern and HRV Analysis for Emotion Recognition System. The annual IEEE International Conference on Computational Intelligence in Bioinformatics and Computational Biology (CIBCB 2016), Chiang Mai, Thailand.)

In addition, a learning part of categorizing is based on continuous adjusting of the neural computing parameters according to the tracking history of several sensor signals, individually for each mother or baby caregiver. Both short term (minutes and even hours) and long term (days, months and even years) tracking history is useful in the learning algorithms. Tracking of the mother's emotional status results in an emotional status graph as a function of time.

In addition, it is possible to track the mother's sleep levels, too, similarly to the baby's ones. In this case the mother should wear the sensors continuously and the signals must be available from all rooms of the home and in an advanced case of the disclosed embodiments from outdoor and long distances, too. The sleep levels are categorized advantageously to the same categories as the baby's sleep levels: a REM and four NREM levels. However, the aspects of the disclosed embodiments are not limited to one categorization. The idea is to measure from the baby as well as from the mother the depth of the sleeping as a function of time (or on certain optimally set time instances only).

In an advanced version of the disclosed embodiments also the spouse or father (or any second caregiver of the baby) can carry the sensors and also his emotional status and sleep levels are tracked and the system can decide according to intelligent algorithms, which one of the parents is at a certain instance a better choice to alarm to care for the baby. This decision depends on the sleep/activity status of the baby at present and in close history and the sleep/emotion status of the parent at present and in close history. The one who is sleeping lighter is the better choice unless he/she has already been sleeping lighter for too long of a period before the present moment and would be to tired to care the baby and may be angry, too. The spouse can also be alarmed, when any other intelligent comparison shows that it is optimal for the whole family to alarm the spouse instead of the mother. The alarming means advantageously provide vibrations on the user's skin so that it is possible to alarm one of the parents without disturbing the sleeping of the other one.

In addition, according to the aspects of the disclosed embodiments the environmental properties of the baby caring room are measured and tracked by conventional smart home sensors like the presence of anybody in the room, temperature, humidity, air pollution, distinct sound, noise and radiation sensors.

The baby, mother and room sensors are also used to automatically measure and track manual baby care actions. For example, a movement sensor can track the presence of the mother in the care room, platform acceleration sensors can sense laying down of the baby on the platform, platform microphones can sense sounds coming from the baby sucking the feeding bottle, the mother acceleration sensors can sense breast-feeding of the baby, and the mother microphone and arm movement sensors can hear and detect the burping action of the baby.

The aspects of the disclosed embodiments comprises also means and a system to generate voice, mechanical vibrations and movements, heating and cooling, airflow and smell to be induced from the platform on the bottom of the place where the baby is sleeping or cared and accessories connected to the platform. These functions are controlled by a control unit, which gets its commands and control data from the Baby Caring Action Database (shortly BCA-DB), according to the action function generated from many sensor data and their processing system.

According to the disclosed embodiments the tracked baby's sleep/activity graph data and mother's sleep/emotion graph data are fed into an Artificial Intelligent Unit (shortly AI unit). The AI unit processes the above-mentioned two graph data and tracked data from environmental room sensors. In some special cases of the disclosed embodiments, the AI unit can also utilize tracked data of some of the baby sensors and mother sensors directly.

In the aspects of the disclosed embodiments, the AI unit analyzes the baby's sleep/activity graph according to given algorithms, aiming to find rhythms and similarities as a function of time. In a similar way the AI unit analyzes the mother's sleep/emotion graph according to given algorithms, aiming to find rhythms and similarities as a function of time. The two graphs, their first and second time derivatives, found rhythms and similarities, as well as the correlations between the two graphs, correlations between first and second derivatives of the two graphs, as well as tracked data from environmental room sensors and events in them are used as features in data mining for finding the best mechanical, voice, heating or cooling and airflow actions to help the baby to move from one sleep/activity level to another, for example, to calm down to fall asleep.

Concretely, the aspects of the disclosed embodiments comprise "a baby nest" where the mother lays the baby to rest. In the mother's lap, the baby has felt skin heat and mother's scent and mother's heart beat and breathing airflow, smell (odor) and voice and got the feeling that mother is there, alive and loving.

When laid on the platform, the change of emotional status resembles a situation when the baby was born and had to leave the heat, movements and sounds of the familiar uterus during the nine months. When the simulated heartbeat keeps going and the baby can feel the mother's warmness, breathes and hums, it feels good to the baby and the change is not too bad.

When the mother leaves the baby in the nest, the platform creates vibrations, sounds, heating or cooling and airflow with temperature and smell that imitate warmth, heartbeat and breathing of the mother, i.e. complete presence of the mother. The utilized signals may be online signals, but they can also be previously recorded signals. When the baby falls asleep, the audio/motion/airflow actions and heating/cooling action will gradually fade away, and so the baby will not become too addicted to the audio/motion/airflow and heating/cooling actions.

During the baby falling asleep, the AI unit tracks changes in the baby sleep/activity level, the mother's sleep/emotion status and the room environment sensor signals, and if the falling asleep (from Drowsy level to REM level) happens smoothly and also moving to deeper sleeping levels (to NREM1, NREM2, etc.) happens smoothly, the AI unit saves into its learning history memory that the used movement and voice action pattern, combined with the platform temperature and airflow temperature, smell and cyclic properties are good to the baby when happening during the mother's emotional status of this time. If the baby wakes back up to the Drowsy or even Morose or Panic level, the AI unit starts to try with another action pattern, which it has learned earlier in a similar situation.

When the baby, after sleeping a while, wakes up and starts to move, but it is yet not a mealtime, those audio/motion/airflow and heating/cooling actions can be switched back on and their intensity and frequency can be adjusted automatically based on baby movements and voice, according to the earlier learned way. The baby nest on the platform can also swing and tighten the baby nest around the baby to increase the feeling to be in the arms of the mother. In addition, extra heating can also be arranged to radiate from the platform to get even more feeling of being in the mother's lap.

The aspects of the disclosed embodiment comprise a substantially rigid and flat platform, an electromechanical transducer attached into the platform, an amplifier providing amplified electronic signals for the electromechanical transducer, an audio/motion player circuitry, an airflow blower circuitry and ventilation elements, a database for audio/motion/airflow files providing electronic audio/motion/airflow action signals for the amplifier and the airflow blower circuitry, a control means to control the audio/motion/airflow player circuitry, the Artificial Intelligence unit (AI unit) and a self-contained power supply for the amplifier and the audio/motion/airflow player circuitry. The platform comprises the many sensors needed in measuring and tracking functions. In addition, the platform comprises heating and cooling elements to adjust the temperature of the mattress to be optimal for baby and the above mentioned ventilation elements to blow the heated and odored (mother's smell etc.) air periodically towards the baby face. In another version of the disclosed embodiments one or more of the circuitry (hardware) parts can be outside of the platform and connected to the circuitry on the platform by wired or wireless links. A part of the sensors can also be on the sensor sheet between the baby and the mattress, and connected a wired or wireless connection to the platform system. According to the disclosed embodiments the platform is placed under the mattress of the baby nest.

The platform comprises two substantially parallel plates, an upper plate and a lower plate, and a frame on which the plates are attached. The size of the platform is advantageously approximately same as the size of the mattress for a baby and the thickness is advantageously between 10 mm and 30 mm, while the thickness of the plates is advantageously less than 5 mm. The material of the upper plate is advantageously plywood with density between 600 kg/m$^3$ and 700 kg/m$^3$ (2.5-3.0 kg/m$^2$ with thickness of 4 mm) and the modulus of bending elasticity along the fibers of the surface layers between 12 and 17 kN/mm$^2$ to provide the desired sound characteristics and motion effects according to the disclosed embodiments.

The electromechanical transducer is attached tightly, by gluing, screwing or other means, inside the platform on the lower surface of the upper plate so that it stimulates bending waves on the plate. The bending waves generate acoustical and mechanical vibrations simulating the mother's intrauterine heartbeat sounds and vibrations, and those audible sounds and mechanical vibrational impulses are transmitted through the mattress to a baby laying in the bed.

The AI unit comprises data handling and processing circuitry and software.

The control unit comprises user interface buttons, including an on-off switch, a manual volume control, a manual audio/motion/airflow file selector and other manual controls.

The sensors are divided in four sensor units: Platform sensors, Sensor sheet, Mother sensors and Room sensors. Platform sensors and Sensor sheet sensors together are later called Baby sensors. The platform sensors are used to monitor the emotional condition and sleep of the baby by detecting for example presence, motions, voice, heart rate, breathing rate, sounds from lung and respiratory track and temperature changes of the baby. The sensor sheet sensors are used to measure ECG, EEG, EMG, SDA (skin dermal activity), skin conductivity, temperature, humidity, etc. signals. In an advanced version of the disclosed embodiments the sensor sheet can also comprise infrared emitters and sensors for brain activity, particularly oxygen saturation, a n d sensing by means of a known NIRS (Near Infrared Spectroscopy) method. The platform sensors and sensor sheet sensors provide sensor data as input for the processing software, which calculates the activity/sleep graph of the baby based on the sensor data by using an adaptive and learning algorithm, to select the best matching audio/motion/airflow and heating/cooling actions signal file and to adapt at least their volume and the periodicity based on the sleep/activity status of the baby.

The Mother sensors unit comprises means for real-time sensing of mother's emotions, including for example, sensors to monitor mother's heart rate and breathing rate and to analyse mother's mental status from microphone signals (humming, singing lullabies etc.) and an adaptive and learning algorithm to process and track mother's emotional status graph, which is used to select and adapt in real-time for example the volume and periodicity of the selected audio/motion/airflow actions in the AI unit. The type and settings of the audio/motion/airflow actions calculated on the basis of the emotions of the mother are stored into a memory storage so that the control system can select and continue playing the same audio/motion/airflow actions after the mother moves off from the baby.

The Room sensor unit measures environmental conditions in the room including microphone and sensors for light, air temperature, air humidity, air pollution, radiation, etc. smart home variables. The room sensors can also be installed or connected on the platform, which is useful, if the care room is not provided with the smart home technology.

In addition to sensing the emotional status of the mother the same mother sensors can be used to record intrauterine acoustic and mechanical vibrations for the audio/motion/airflow data files. For these recordings, also microphones, ultrasonic Doppler sensors and stethoscope sensors, and other well-known technology can be used to store acoustical and mechanical vibrations from the mother's body and uterine in different emotional conditions and after or during the last months of pregnancy. Breathing rate and style can also be measured with these sensors and use the data in adjusting the warm air blowing rhythm and style. These recordings can also include the mother's lulling and humming voices and singing of lullabies.

The invented system comprises several innovative steps to enable the baby to sense improved sensation of mother's presence with intrauterine heartbeat sounds, warmness of the mother's lap and familiar ventilation and sound environment, and to provide an adaptive and learning system for enhancing emotional interactions as well as calming and inducing sleep for a baby. While establishing the aspects of the disclosed embodiments on recording of the baby's activity/sleep levels and graph and so defining his/her daily rhythm and controlling the given treatment based on learning principles, the aspects of the disclosed embodiments are not obvious for the skilled person in view of the prior art or the state of the art in general. In addition to the learning and adaptive system to select and control the audio/motion/airflow actions, the aspects of the disclosed embodiments provide a uniformly radiated combination of sound and motions generated by the bending waves. The sound and movement is emitted from substantially the whole area of the mattress and the airflow comes to the faces of the baby although it is heated and blown from the platform. The sensation effect, design, practicality and other benefits provided by the aspects of the disclosed embodiments could not be achieved by a straightforward combination of the prior art, and thus the innovation provides unexpected effects in view of the prior art. In addition, the device according to the aspects of the disclosed embodiments is a new product type on the market and other similar solutions do not exist at present.

Other features of the aspects of the disclosed embodiments will become apparent from the following detailed description considered in conjunction with the accompanying drawings. It is to be understood, however, that the drawings are designed solely for purposes of illustration of the invention, not to limit its variations.

DETAILED DESCRIPTION

In the following detailed description, numerous specific details are set forth in order to provide a thorough understanding of the aspects of the disclosed embodiments. However, it will become obvious to those skilled in the art that the aspects of the disclosed embodiments may be practiced without these specific details. The description and representation herein are the common means used by those experienced or skilled in the art to most effectively convey the substance of their work to others skilled in the art. In other instances, well known methods, procedures, and systems have not been described in detail to avoid unnecessarily obscuring aspects of the disclosed embodiments.

Figure 1:
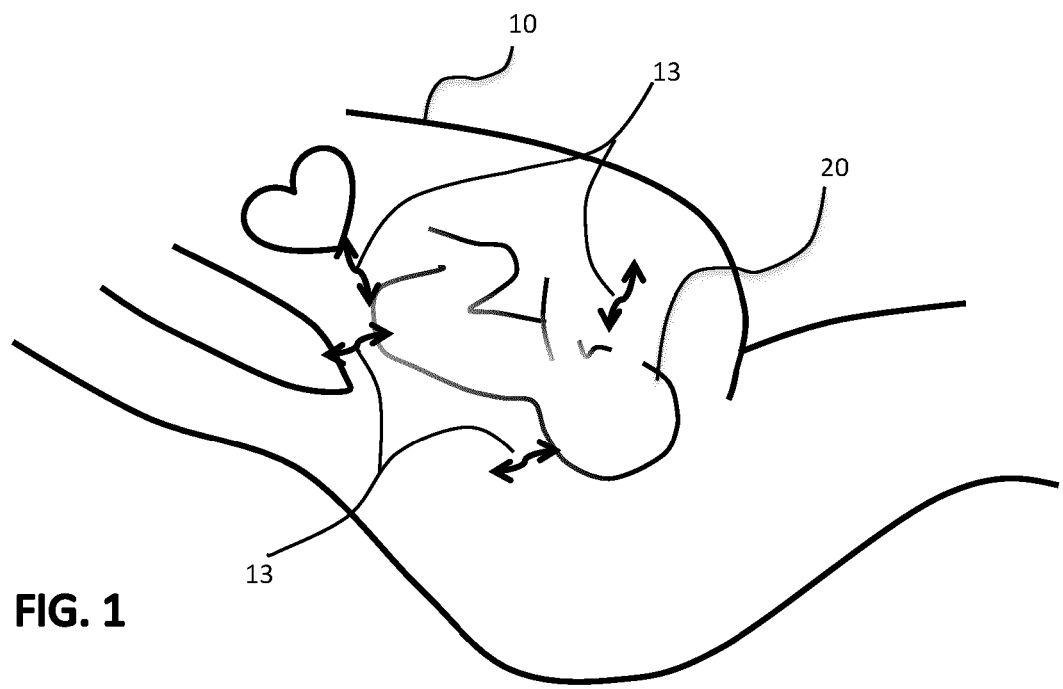
FIG. 1 shows interactions between a mother and a baby during pregnancy.

In FIG. 1 a mother 10 and her fetus 20 in the uterus are depicted. When the fetus 20 is in the uterus different kinds of interactions 13 between the mother 10 and fetus 20 are intimate and real-time. The fetus hears and senses mothers' heart and respiratory fluctuations in the uterus. Also the mother senses fetus movements. Biochemical and hormonal changes affects also in both directions. Therefore, physical, emotional and even psycho-somatic interactions could be said to be present when the fetus 20 is in the uterus of the mother 10.

Figure 2:
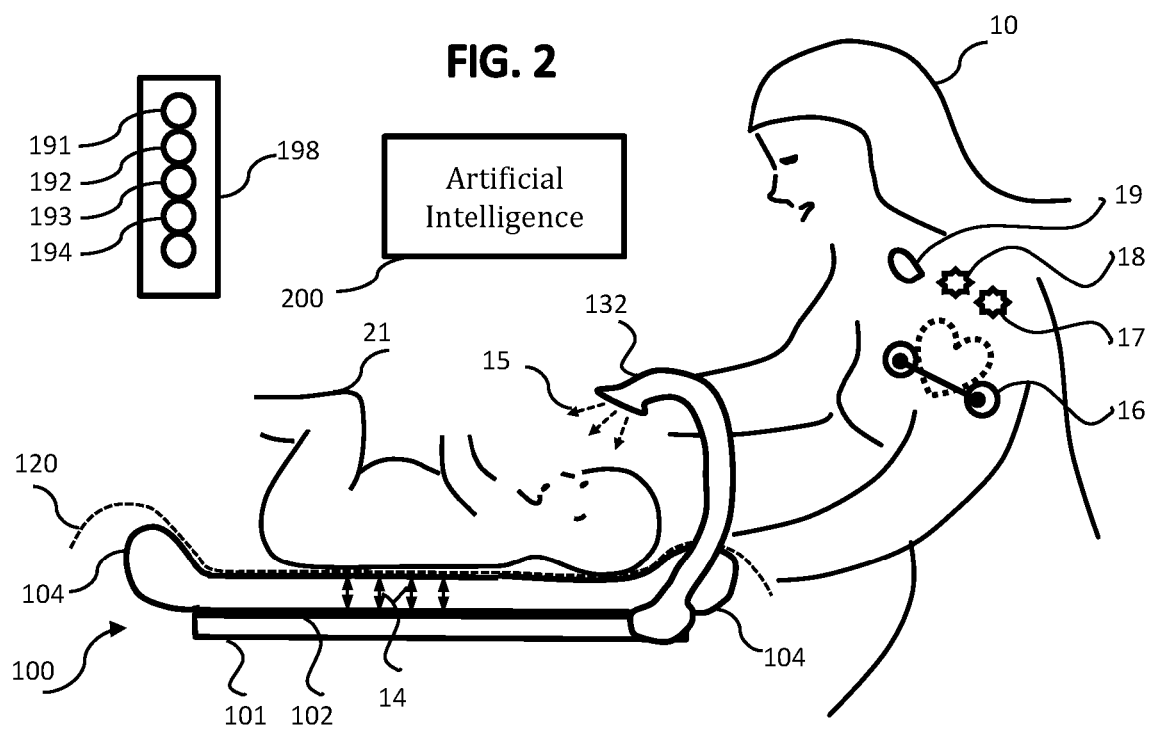
FIG. 2 shows interactions between a mother and a baby after birth by using an embodiment of the present disclosure. Also an Artificial Intelligence unit and part of the sensors are seen in FIG. 2.

FIG. 2 describes interactions between the mother 10 and her baby 21 after birth by using the baby caring device 100 according to the present invention. The mother's heart and respiratory sounds and motions are recorded by a heart sensor 16, microphones 17, body motion sensors 18 and other bioelectronics sensors 19 attached on her body, processed in the Artificial Intelligence unit 200 (AI unit) of the present invention. The sensors and microphones on upper plate 102 of the platform 101 and the sensor sheet 120 of the baby caring device 100 are used to measure the sleep/activity data of the baby. The baby data is further processed in the AI unit 200 to indicate a status of the baby, which is further combined with the data from Mother's sensors and used to optimally adjust the audio/motion/airflow actions 14 and 15 to be emitted from the upper plate 102 and the airflow pipe 132 of the platform 101 to match soothing and calming of the baby in the best way and give the baby better emotional feelings.

More accurately, the mother sensors can be any combination of sensors, including heart sensors (16), microphones (17), movement sensors (18) and bioelectric sensors (19), which are used to measure and track any combination of the following: mother's or other caregiver's body and arms movements, body temperature comprising fever and daily variations of the body temperature, heart activities comprising pulse and ECG, lung activities comprising breathing rate and airflow curve, pauses, blood circulation comprising oxygen saturation, flow volume, blocks, body temperature distribution, brain activities comprising EEG, oxygen saturation, muscle activities comprising EMG, skin activities comprising conductance, sweating, gastro/metabolic activities, speaking, humming, singing, breathing, sighing, environmental sounds coming from the home life, other children, kitchen machinery and outdoor traffic.

In addition, in FIG. 2, there are a Room sensor unit 198 for measuring environmental conditions in the baby caring room or place including microphones 191 and sensors for light 192, temperature 193, humidity 194, etc. smart home variables, which are used to measure and track any combination of the following: presence of anybody in the room, temperature, light, humidity, air pollution, distinct sound, noise and radiation. In another embodiment of the aspects of the disclosed embodiments, the room sensors 198 are integrated to the platform 101. This version is useful in houses where smart home technology is not available.

Figure 3:
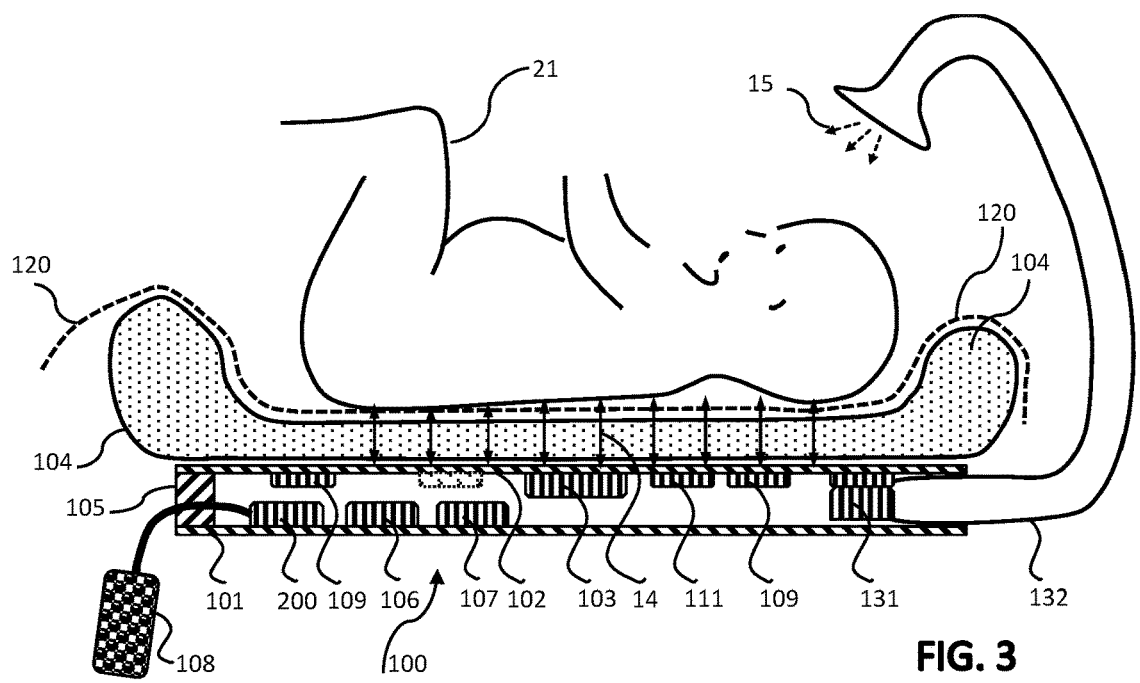
FIG. 3 shows a cross section side view of a baby caring device according to one embodiment of the present disclosure.

FIG. 3 shows a cross section side view of the baby caring device 100 in accordance with an embodiment of the present disclosure. The baby 21 lays on the device 100, which comprises a mattress 104 with a baby nest, a platform 101, an upper plate 102, at least one electromechanical transducer 103 that is attached to the lower surface of the upper plate 102, a lower plate, a frame 105 attached between the upper plate and the lower plate, a power supply 106, an audio/motion player circuitry 107, AI unit 200 and the control unit 108. The ventilation blower 131 is inside the platform, including the cyclic blower and air heater, humidifier and odoring means. A flexible pipe 132 brings the cyclic airflow on the baby's faces.

The upper plate, lower plate and frame construct a substantially rigid and flat platform 101. The electromechanical transducer 103 is attached advantageously substantially on the center of the upper plate 102. In addition, on the upper plate 102 of the platform 101 there are one or more movement sensors 109 and microphones 111. The control unit 108 advantageously comes outside of the platform to provide user interface buttons that are easily handled. The control means 108 are advantageously connected either with wires or wirelessly to the audio/motion player circuitry 107 and other units inside the platform. The control unit 108 with user interface buttons can also be integrated into the platform frame 105. The mattress 104 is advantageously integrated within a comfortable baby nest with soft boundaries. The sensor sheet 120 is on the mattress 104 right under the baby.

Figure 4:
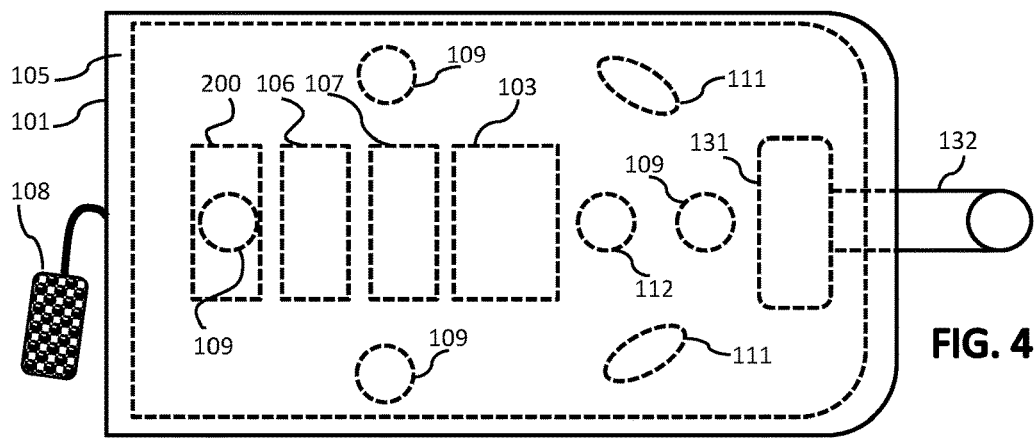
FIG. 4 shows a cross section top view between the hard platform and soft mattress of a baby caring device according to one embodiment of the present disclosure.

FIG. 4 shows a cross section top view of the baby caring device 100 shown in FIG. 3.

The motion sensors 109 are attached to upper plate 102 to indicate and measure movements of the baby 21. Heart and breathing rates of the baby 21 are advantageously picked up from those signals. Also other sensors 112 for measuring temperature, humidity etc. may advantageously be part of the device 100. Some sensors are advantageously fixed on the upper surface of the upper plate 102 of the platform 101 to get closer contact to the baby.

The microphones 111 listening to the babbling, crying, joggling, talking, breathing, urinating, excreting, farting, burping and silence or other voices of the baby 21 are also advantageously attached to the upper plate 102 near the head of the baby 21.

The ventilation blower 131 with the flexible pipe 132 can also be seen right in FIG. 4.

In a simple but advantageous operating mode the baby 21 is laid on the mattress 104 and an appropriate audio/motion file with the desired volume is selected by using the user interface buttons of the control unit 108. After that the audio/motion player 107 is switched on to play the audio/motion file. Electronic signals based on the audio/motion file is amplified by the amplifier and fed to the electromechanical transducer 103, which stimulates bending waves on the upper plate 102 and further generates audible sounds and mechanical vibrational impulses to calm and soothe the baby. After the baby has fallen asleep, the audio/motion player 107 is advantageously switched off.

Figure 5:
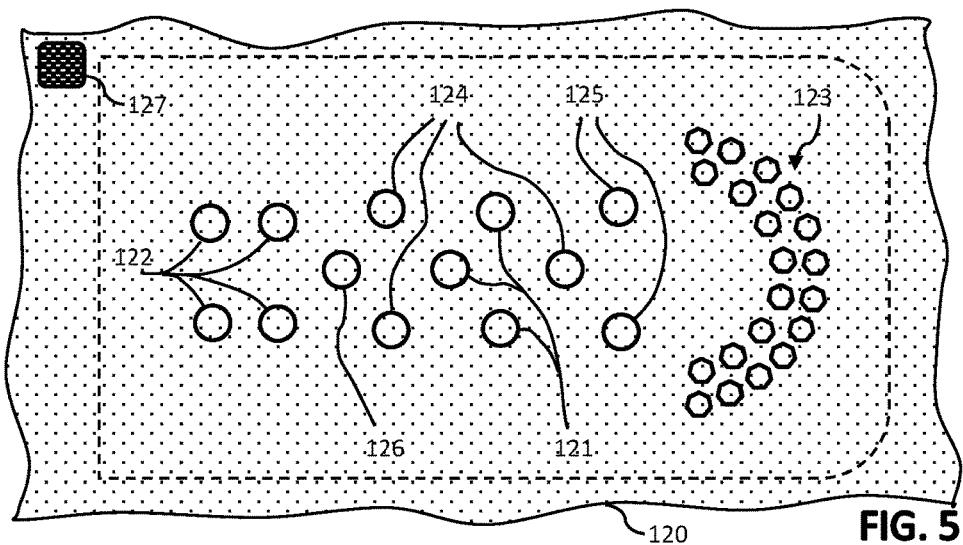
FIG. 5 shows a cross section top view on the sensor sheet level of a baby caring device according to one embodiment of the present disclosure.

FIG. 5 shows a cross section top view on the sensor sheet 120 level of a baby caring device 100 according to the aspects of the disclosed embodiments. The sensor sheet 120 may advantageously comprise of a set of special sensors, which advantageously measure bio-signals such as ECG 121, EMG 122, EEG 123, SDA (skin dermal activity) 124, oxygen saturation, skin conductivity, skin temperature 125, humidity, moisture, urinating etc.

The sensor sheet 120 is put on the mattress 104 and the baby is laid without clothing or with minimum clothing on the sensor sheet to get skin conduction to the sensors. The sensors are connected to the audio/motion circuitry with wires or wirelessly. In an advantageous embodiment of the present disclosure a wireless communication module 127 is placed on a corner of the sheet, which can also be the place where the wires, if needed, are connected to. The wireless communication module 127 has the counterpart module in the platform 101 advantageously close to AI unit 200.

In another embodiment of the present disclosure the movement sensors 109 or microphones 111 or both are placed on the sensor sheet 120 to get better signals, when the acoustic and physical signals do not need to go through the mattress 104.

Concluding with the baby sensors, the baby sensors fixed on the platform can be any combination of movement sensors (109), microphones (111), and temperature, humidity and chemical sensors (112), which are used to measure and track any combination of the baby's presence, motions, voice, heart rate, breathing rate, sounds from lung and respiratory track, temperature changes, baby's crying, joggling, talking, breathing, urinating, excreting, farting, burping and silence. The baby sensors on the sensor sheet (120) under the baby laying on the baby care device (100), can be any combination of sensors of ECG (121), EEG (123), EMG (122), SDA (124), temperature (125), humidity (126), infrared, NIRS, Oxygen saturation, chemical and movement sensors and microphones, which are used to measure and track any combination of ECG, EEG, EMG, SDA, oxygen saturation, skin conductivity, skin temperature, humidity, urinating, excreting, farting, silence.

Figure 6:
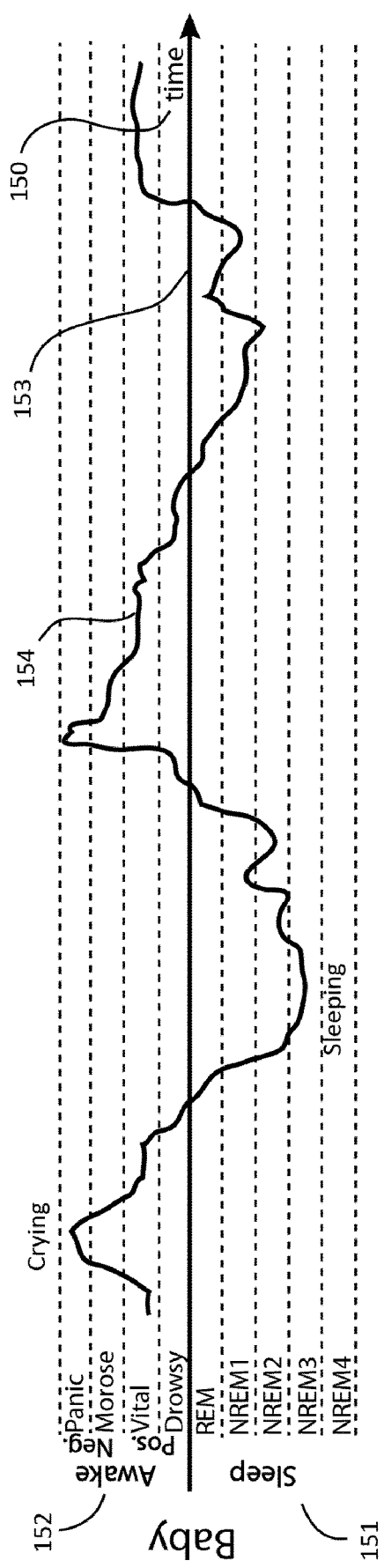
FIG. 6 shows an example of the daily rhythm of the baby explained by means of sleep/activity level graph as a function of time.

FIG. 6 shows an example of the baby's sleep/activity graph as a function of time 150 with five known sleep levels 151 and four activity levels 152. Its x-axis 153 indicates the border between awake and sleep statuses. The upper part of the x-axis reflect s the more active the baby is, and the lower part of the x-axis reflects the deeper in sleep the baby is. It is also possible to use another order of the activity or sleep levels. The curve 154 tells the baby status as a function of time. It reveals also a sleep/awake rhythm of the baby.

Figure 7:
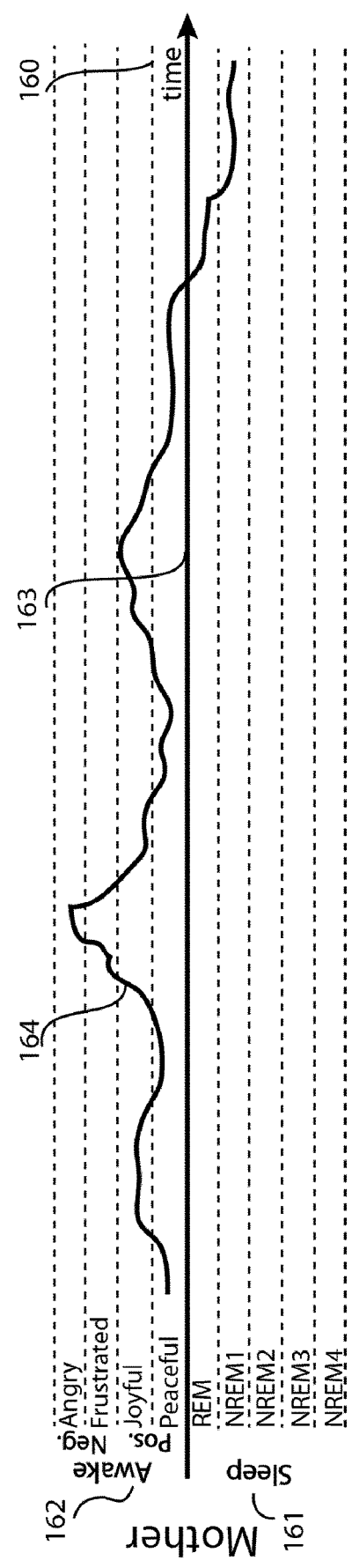
FIG. 7 shows an example of changes in emotional status of the mother explained by means of sleep/emotion status graph as a function of time.

FIG. 7 shows an example of the mother's sleep/emotion status graph as a function of time 160 with five known sleep levels 161 and four emotional statuses 162. The emotional statuses (called further also emotional levels) are, as described earlier, Peaceful, Joyful, Frustrated and Angry. There can be more emotional statuses, which can be arranged so that the upper part of x-axis 163 reflects that the status is more negative and more aggressive the mother's emotional status is. The sleep levels are arranged similar to baby's sleep levels so that the lower part of the x-axis reflects the deeper in sleep the mother is. Also here it is possible to use another order of the emotion statuses or sleep levels. The curve 164 tells the mother's sleep/emotion status as a function of time.

The baby's sleep/activity levels and the mother's sleep/emotion status can be selected in many different ways. The choices in FIGS. 6 and 7 are only examples of many different alternatives. The aspects of the disclosed embodiments consider how these kind of measures can be utilized to optimize baby-mother emotional interaction after birth in the method and system described herein.

Figure 8:
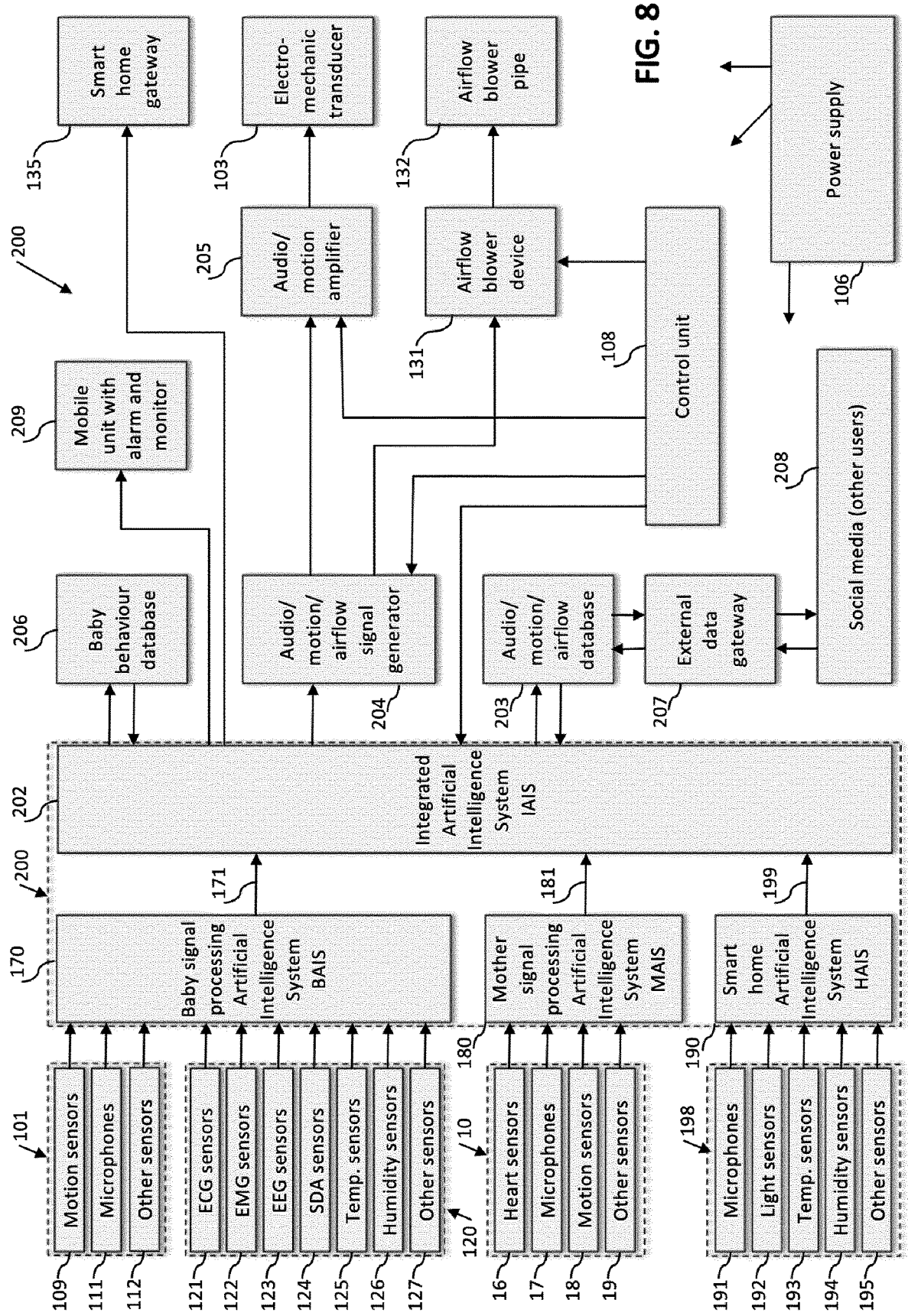
FIG. 8 shows a block diagram of the electronic and information technique system of the present disclosure.

FIG. 8 shows a more detailed block diagram of the electronic and information technique system of the aspects of the disclosed embodiments.

From left the sensors are seen in four blocks: The movement sensors 109 (acceleration and gyro sensors), microphones 111 and other sensors 112 (for example temperature or humidity sensors) on the upper plate 102 of the platform 101; the ECG 121, EEG 123, EMG 122, SDA 124, temperature 125, humidity 126, and other sensors on the sensor sheet 120; the heart sensors 16 (heartrate, ECG and/or heart sound sensors), microphones 17, movement sensors 18 (acceleration and gyro sensors) and other sensors 19 (e.g. other bioelectric, infrared or NIRS sensors) attached to the mother; and the room sensor unit 198 with microphones 191 and sensors for light 192, temperature 193, humidity and other 194 smart home parameters.

The AI unit 200 consists of four modules: a Baby signal AI 170 (BAIS), a Mother signal AI 180 (MAIS), a Smart-home signal AI 190 (HAIS) and an Integrated signal AI 202 (IAIS).

The Baby signal conditioning and data aggregation AI system 170 (shortly BAIS) receives the sensor signals from first two sensor blocks, including sensors on the platform 101 and on the sensor sheet 120. BAIS amplifies, filters and converts them to digital data, aggregates and combines the sensor data to higher level variables such as, movement activity, crying volume, heart rate, breathing rate, body temperature, sweating level, etc. as a function of time. By using, for example, artificial neural network processing or decision tree algorithms, BAIS 170 combines the generated data to the baby sleep/activity level data 171, which respects the baby sleep/activity graph function 154. This processing can be simple data combining or, in an advantageous case, complex machine learning process in an artificial intelligence processor set.

A Mother signal conditioning and data aggregation AI system 180 (shortly MAIS) receives the sensor signals from the third sensor block, including the heart sensors 16, microphones 17, movement sensors 18, bioelectric sensors 19 and possible more sensors attached to the mother 10. MAIS 180 amplifies, filters and converts them to digital data, aggregates and combines the sensor data to higher level variables such as speech style, relaxation of voice, movement activity, heart rate, breathing rate, etc. as a function of time. By using, for example, artificial neural network processing or decision tree algorithms MAIS 180 combines the generated data to the mother's sleep/emotion status data 181, which respects the mother's sleep/emotion graph function 164. This processing can be simple data combining or, in an advantageous case, complex machine learning process in an artificial intelligence processor set.

The Smart-home environmental signal conditioning and data aggregation AI system 190 (shortly HAIS) receives the sensor signals from the fourth sensor block 198 (the room sensors), including microphones 191, light sensor 192, temperature sensor 193, humidity sensor 194 and possible more sensors 195 of the smart home system. HAIS amplifies, filters and converts them to digital data, aggregates and combines the sensor data to higher level smart home data 199 such as room quietness, presence of other family members, distinct sounds, room temperature, luminosity, air quality and some more variables, which are used as extra parameters in further data processing phases.

The Integrated artificial intelligence system 202 (shortly IAIS) comprises processors, algorithms and memory parts to store and drive the software to handle data in a smart way, namely, the baby's sleep/activity data 171, mother's sleep/emotion status data 181 and smart home data 199; by using baby behavior data from Baby behavior database 206, audio/motion/airflow signal files and breathing signal files from Audio/motion/airflow database 203 and algorithms, commands and controls from the Control unit 108. IAIS 202 calculates (selects and modifies) the audio/motion/airflow data file, feeds it to Audio/motion signal generator 204, which controls its volume and periodicity according to the commands and controls from the Control unit 108, converts it to analog signal and feeds to the Amplifier 205, which amplifies it according to control from Control unit 108 and feeds to Electromechanical transducer 103. IAIS 202 generates also the data for the breathing airflow blower generator 131 to control temperature, humidity and odor of air and its streaming power and periodical properties from the blower through the pipe 132.

Alarming and monitoring unit 209 is used when IAIS results the need to call the mother or nurse. It is also used to follow up sleeping or activity level of the baby and to display predicted wake up time. Advantageously, Alarming and monitoring unit 209 applies conventional mobile phone or smart watch technology. In an advanced version of the disclosed embodiments a separate wireless vibrating alarm actor is combined to the mother's sensor unit and so is in direct touch with the mother's skin. IAIS sends also data to control smart home appliances, dimming of lights, adjusting the room temperature, controlling the air quality, etc. using the Smart home gateway 135.

The power supply 106 gives electric power needed in the other parts of the circuitry. The Audio/motion/airflow database 203 communicates with social media users 208 via an External data gateway 207. The audio/motion/airflow files can be delivered to other users of the similar baby caring devices; and the audio/motion/airflow files can be received from other users. In an advantageous form of the aspects of the disclosed embodiments the Baby behavior database 206 is connected to other users via the same or similar gateway.

The Baby behavior database 206 stores the user's baby's personal day and week rhythms, including at least sleeping behavior, eating times and playing periods. The behavior data is automatically collected during the use of the baby caring device 100 and the behavior patterns are continuously sharpened according to the collected and aggregated sensor data.

The Audio/motion/airflow database 203 stores versatile set of audio/motion/airflow files, which can be files recorded and formulated from the baby's, mother's and room sensors in different hours of day, different emotional statuses, and during different baby caring activities (feeding, massaging, washing, dressing etc.), and have been found effective to calm and soothe the baby. The stored audio/motion/airflow files can also be files, which have been received from other users of the similar devices applying the aspects of the disclosed embodiments, and have been recommended by other users. The stored audio/motion/airflow files can also be files, which have been generated artificially for the calming or relaxing use, relaxing music files, or any audio/motion/airflow files which have been found effective to relax, calm or improve babies' emotional condition.

An example, how the audio/motion/airflow file can be formulated from the sensor signals: During breast-feeding the mother uses the sensors 16 and 17, which record her heart rate from simple ECG signal and heart sound (as stethoscope signal), breathing rate and breathing sound (by microphone). The recording is changed to the audio/motion/ airflow file by filtering and balancing the sound frequencies. And the rhythm of the airflow from the breathing airflow generator 131 can be synchronized with the breathing sound. Or alternatively, a standard heart/breathing sound with the airflow cycle file is modified according to measured heart rate, heart rate variations and breathing rate.

As an example of how the platform sensor signals can directly be used to select and adjust the right audio/motion/airflow file: The BAIS 170 calculates variable values from the motion sensors 109 signals. For example, motion signals (acceleration from head, feet, left and right sensors) can result in an average acceleration level, which gives a sleep/awake variable. Acceleration signal from the feet sensor only gives a wincing variable, acceleration from the left and right sensors gives a spinning variable, acceleration from the head sensor gives a head twirling variable (trying to find a nipple). Microphone 111 signals give another sleep/awake variable, which is analyzed from breathing, babbling, crying and other voices of the baby. Different motion and voice patterns can be used to evaluate the baby's awareness level. They can directly be used by comparing their height to given threshold parameters used in selecting a suitable audio/motion/airflow file from the database. They can also be used to adjust its volume on a sufficient level to optimally match with the awareness level of that moment. Awareness level is only an example of the resulting variables. Other examples are sleep depth, activity level, cheerfulness or sadness.

In advanced arrangements bio-signals (ECG 121, EEG 123, SDA 124, for example) can be used to formulate audio/motion/airflow actions by adjusting, for example, heart sound frequency and clearness (signal-to-noise-ratio) according to baby's heart rate or brain wave frequencies. The system can also be a learning system so that, when certain audio/motion/airflow actions are found to give good results in soothing or calming the baby and leading to respective sensor signal combinations, the same audio/motion/airflow files are used next time when similar sensor signal combinations exists. Also these good experiments can be stored and shared in social media between different babies. This can happen advantageously via social media groups of the users.

Figure 9:
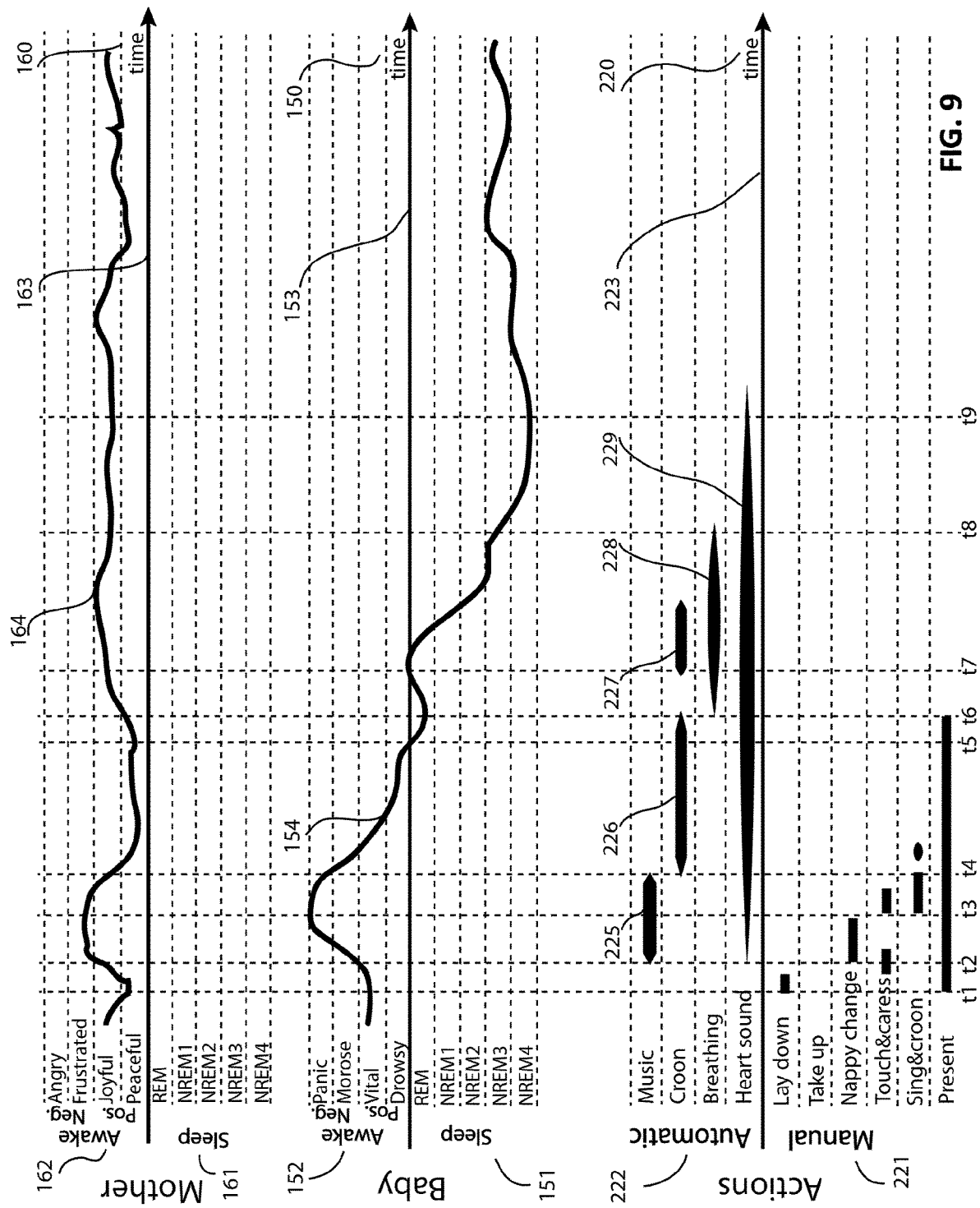
FIG. 9 shows an example of how measured baby's sleep/activity graph and mother's sleep/emotion graph are used to produce audio/motion/airflow actions as a function of time during baby caring activities.

FIG. 9 shows an example how the baby's sleep/activity graph 154 (FIG. 6), generated by BAIS 170, and the mother's sleep/emotion status graph 164 (FIG. 7), generated by MAIS 180, join to manual actions 221 of the mother and the automatic actions 222 generated by IAIS 202.

In this example, mother's manual actions can be as follows: to be present/absent in the care room (marked as Present in the FIG. 9), to lay the baby down on the baby nest 104 (Lay down), to take baby up from the baby nest 104 (Take up), to change the baby's nappy (Nappy change), to touch and caress the baby (Touch & caress), to sing and croon to the baby (Sing & croon), feeding by a baby bottle, giving a pacifier, giving vitamins, breast feeding and burping by taking the baby in the mother's lap, etc. Speaking to the baby is also an action, which normally happens all the time when the baby is awake and active. Although it is not mentioned in FIG. 9, the mother's microphones 17 are listening and tracking mother's voice all the time.

In this example, automatic sound, mechanic and airflow actions 222, generated by the IAIS 202 on and from the platform 101, can be as follows: to play music 225 (Music), to play crooning voice of the mother (or somebody else) 226 and 227 (Croon), to blow cyclic heated and odored air to simulate mother's breathing 228 (Breathing), to play mother's (or somebody else's) heart sound and/or other sounds and mechanical movements, what the baby has listened and sensed when being nine months in the uterus 229 (Heart sound).

In this example the event chain is as follows: At the time instance t1 the mother comes to the room (Present starts) and lays the baby down to the baby nest 104. The baby is awake and vital (see curve 154 at time instance t1) and the mother is joyful but calming to peaceful status (see curve 164 at time instance t1). She caresses the baby, and at t2 she starts to change the baby's nappy. The baby becomes morose (follow curve 154) and the platform starts to play calming music 225. Also heart sound 229 starts and grows little-by-little. Mother's emotional status jumps up (follow curve 164) to the frustrated level. At t3 the nappy change is ready but the baby cries in panic. Music 225 continues and heart sound 229 grows stronger. The mother starts again to caress the baby and sings or croons. At t4 the baby stops crying, the mother stops to croon and the platform stops the music 225 and starts crooning 226. Volume of heart sound 229 is now strong. The baby calms down and becomes drowsy and falls asleep at t5. Soon after that at t6 the platform stops to croon 226 and the mother goes peacefully out of the room. Simultaneously, the platform starts the breathing simulation 228. At t7 the baby wakes up, moves and cries a little, while the platform starts to croon 227 again. The baby falls back asleep and when reaching the NREM2 level the crooning 227 ends and at t8, when reaching the NREM3 level, the breathing 228 from the platform softly finishes. At t9 the baby is in deep sleep (NREM4) and the heart sound 229 from the platform also softly finishes.

In a simple version of the disclosed embodiments algorithms in the IAIS make decisions, which are based on the real-time values and short-time changes in baby's sleep/activity level graph 154 and mother's sleep/emotion status graph 164. The decisions can be, for example, as follows: 'When the baby turns to the Panic level and begins to cry, and the mother turns to the frustrated level, and there is nappy changing going, switch music on and select a piece number x, which is also mother's favorite piece'. The mother's emotional status is also important to take into account when the artificial intelligence makes the decisions of actions.

The more complex algorithms also utilize history of decisions and follow-up of their effects. Thus, when finding from the two graphs 154 and 164 that the situation is proceeding in a way, which can be found from the history memory, the decision of IAIS is based on that history data. If there are several similar graph patterns, IAIS compares, which of the previously selected action combinations have led to the best results for the next minutes or hours in the baby sleep/active levels, and selects that one.

In an advanced version of the aspects of the disclosed embodiments the artificial intelligence of IAIS utilizes the both graphs 154 and 164, their changes (by using their first and second derivatives), historic data of their relational behavior, and combines smart home data 199 (both values and their changes) and its history data to make even smarter decisions, based on which combination of actions on the platform will lead to the best results for optimal rhythm and shape of the baby sleep/active graph. In an advantageous form of the aspects of the disclosed embodiments, the mother's sleep/emotional status graph is targeted to optimize. The final goal is to improve both the baby's and the mother's wellbeing.

Figure 10:
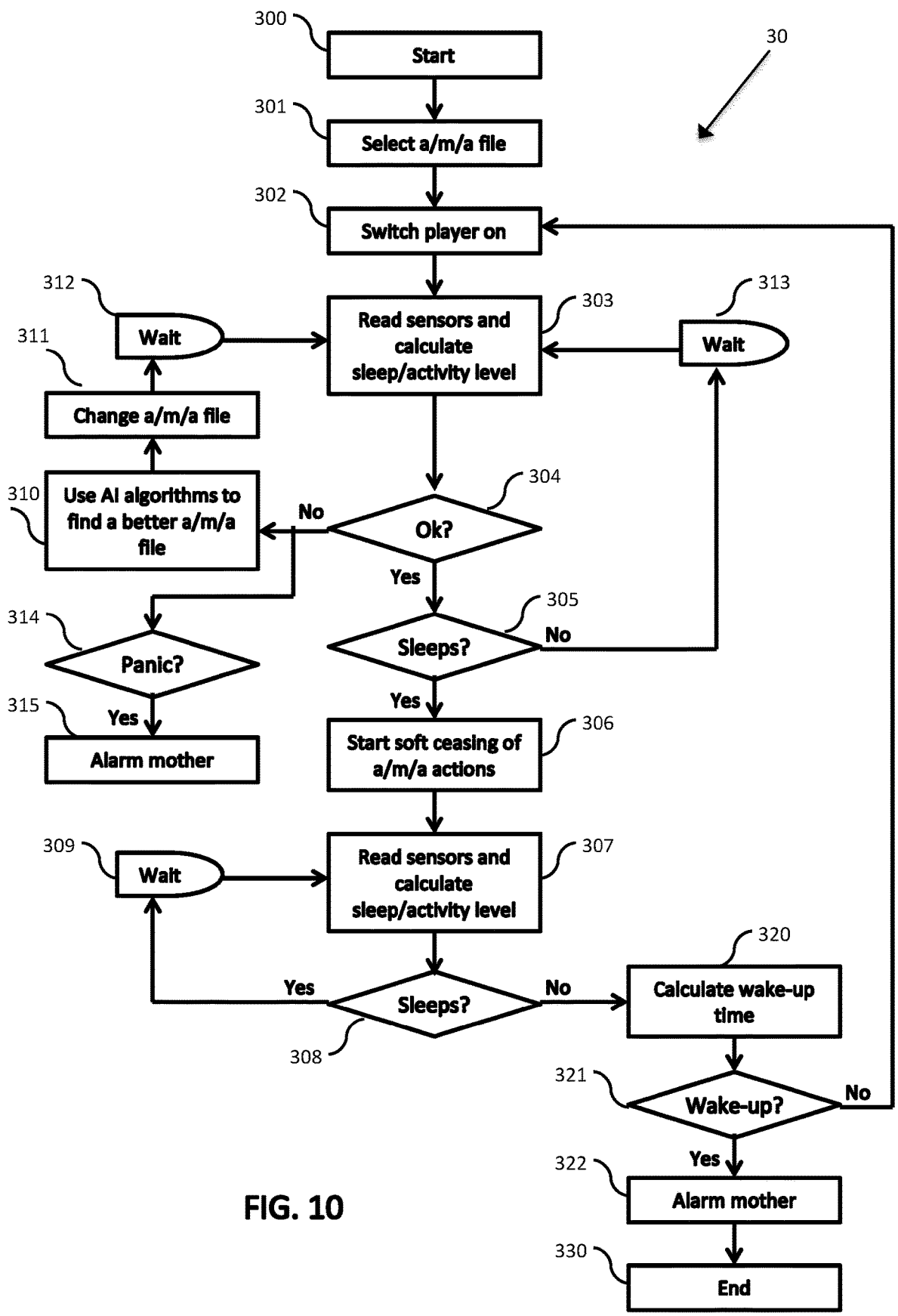
FIG. 10 shows a flowchart of a simplified example of the baby caring processes.

FIG. 10 depicts an example of the operating processes of baby caring with the device and method of the disclosed embodiments. This process 30 as a diagrammatic view handles a situation where the mother comes with her baby to the caring room, lays her baby down to the cradle 100 and takes the device in use by manually selecting the first audio/motion/airflow (shortly as a/m/a) file. It also assumes that the mother sensors have already earlier been used to create the personal a/m/a files for different caring situations. In this case the objective is to get the baby to fall asleep and if he/she awakes too early, try to get the baby to fall asleep again.

FIG. 10 comprises steps where the sensing, monitoring, calming and sleep inducing functions are performed by the intelligent baby care operating process 30 according to the present invention. In the process 30 one or more buttons of the control unit 108 are utilized to initialize the process. The system selects one of the audio/motion/airflow files 301 from the Audio/motion/airflow database 203 and adjusts the volume and periodicity according to the Control unit 108 settings. In one advantageous embodiment of the present disclosure selection and finetuning of the audio/motion/ airflow file is based on real-time analysis of the sensor data from the mother's sensors 16, 17, 18 and 19 (e.g. heart rate and breathing rate in the a/m/a actions are adjusted in real time).

The system switches the audio/motion and airflow actions on 302 and starts to monitor the status of the baby and to provide sensor data as an input for the process in IAIS 202 to produce the audio/motion/airflow data to the Audio/ motion/airflow generator 204. Simultaneously IAIS 202 calculates 303 the sleep/activity status of the baby and the emotional status of the mother based on the sensor data. Therefore, in step 303 the system reads the data from the platform 101 sensors 109, 111 and 112 and the sensor sheet 120 sensors 121-126 to BAIS 170 and calculates periodically the sleep/activity level 154 of the baby in real time. In step 303 the system also reads the data from the mother's sensors 16-19 to MAIS 180 and calculates her emotional status 164. In addition, the data from the room sensors 191-194 can be read in this phase 303 to HAIS 190 and utilized in the calculation of changes in step 310, if needed. This need is checked in step 304 by asking whether the sleep/active level 154 is going to the right direction (down) or not. When answer is not, also another checking is done in step 314, namely if the level 154 is Panic, an alarm is sent to the mother's mobile device 209 in step 315. This is done only when the mother is absent from the caring room, because being present she can see and hear the panic.

After finding a better a/m/a file in step 310, the system adjusts the settings 311 of the audio/motion/airflow generator 204 and thus the played audio/motion/airflow signal is based on intelligent analysis of emotional interaction between the mother and her baby. After using the system longer (days or weeks) the system can also in step 310 utilize historic data to optimize the changes of audio/motion/ airflow actions according to adaptive and learning algorithms. A delay 312 is needed to adjust an optimal rate for periodic checking of the status of the baby. The sensors can collect data continuously with a higher rate for tracking the changes more accurately and for helping to filter erratic measurements caused, for example, from skin contact problems of the moving baby. As soon as in step 304 the baby sleep/activity level 154 is changing in the right direction (down), the system continues to loop with the same audio/ motion/airflow actions through delay 313 and starts to check in step 305, when the level is going down to the REM level (the baby falls asleep).

After the baby 21 has fallen asleep 305, the audio/motion signal generator 204 is softly ceased off in step 306, but the system continues to monitor the status of the baby 21 in step 307. The loop between steps 307, 308 and 309 continues so long as the answer in step 308 is "No", and the process branches to step 320 where a wake-up time of the baby 21 is analyzed. The system calculates in step 320 whether it is time to wake up using Baby behavior database 206 based on the time of day, the duration of the sleep, the duration of the sleep during previous nights and the frequency of previous sleep inducing attempts. If it is not yet time to wake up in step 321, the system switches the audio/motion signal generator 204 on again by returning back to step 302. If the system deduces in step 321 that it is the right time for the baby to wake up, the system alarms the mother or nurse of the baby in step 322. Advantageously, the alarming is done by using a mobile phone or a smart watch. The process 30 ends at step 330.

In an advanced version, the spouse wears similar sensors as the mother and his sleep/emotion graph is also tracked and utilized in optimizing baby care. Thus, for example, when the baby wakes up too early and it is not yet time to breast-feed the baby and new trials to change the audio/ motion/airflow actions does not help to get the baby back in sleep, the system decides to alarm the spouse to care the baby instead of the mother. Also the decision can be done on the basis of comparing the sleep graphs of the parents and wake-up the one, whose sleeping is lighter at present and/or whose sleeping phase has lasted longer before the present time.

Many different kinds of intelligent algorithms can be developed and the system can learn the best way to react when the baby's sleep/activity level graph shows that the help of the parents is needed.

It is also advantageous to use one more algorithm within the process 30, which detects when the baby is sleeping too long due to different reasons: The baby is becoming sick or the baby has been travelling and been awaken for a long period or for some other reason the sleeping rhythm has been confused. In these kinds of situations it is better to wake the baby up for feeding, nap-changing and/or just playing with. Waking the baby up can be executed by the most convenient way by switching on a merry song or recorded speaking or humming of the mother from the platform electromechanical transducer (speaker) 103.

One more advantageous algorithm is needed for SIDS detection and alarming. In SIDS seizure the baby stops to breathe due to unknown reason and needs to be woken up by trembling. This can be sensed by breathing sensing algorithm and an extra SIDS-detection algorithm, which first detects stop of breathing for longer than preset time period (30 to 120 seconds) and then starts a special audio, motion and airflow action with a preset aloud, noisy and strong shaking contents and, if the baby doesn't start breathing again within next 30-60 seconds, sends a preset SIDS-alarm to the mother and possible other caregivers. A similar algorithm can be used also in sleep apnea problems.

Further another embodiment of the present disclosure comprises an operating mode and means to transfer the emotions of the baby's mother and corresponding physical effects to the baby to calm and sooth the baby from distance, for example, when travelling. This means special audio/ motion/airflow actions, which have been recorded for this use only. They might comprise mother's speaking, humming and singing and special smell coming from the airflow system. The mother of the baby can use for example her smart phone or other touch device to express her emotions, which can also be real-time actions and can be transferred via internet to the device 100 according to the aspects of the disclosed embodiments.

Although only the baby's mother has in this text been mentioned as a caregiver, the aspects of the disclosed embodiments are not limited to mother-baby case. Also father, nurse, step-mother and any caregiver can be a user of the aspects of the disclosed embodiments. So the word "mother" in the text must be understood in a wider content meaning also the adoptive mother, step- or foster mother, spouse, biological father, the adoptive, step- or foster father, siblings, nurse or other caregiver.

While there have been shown and described different operating modes and functions of the intelligent baby care operating system by depicting various embodiments, the different operating modes may be combined and functions of them can be used at the same time in the system according to an embodiment of the present disclosure.

While there have been shown and described and pointed out fundamental novel features of the present disclosure as applied to advantageous embodiments thereof, it will be understood that various omissions and substitutions and changes in the form and details of the disclosed embodiments may be made by those skilled in the art without departing from the spirit of the disclosed embodiments. In other words, the aspects of the disclosed embodiments may vary within the scope of the claims.

The invention claimed is:

1. A baby care arrangement for helping a mother or another caregiver with her/his baby to find an optimal life, sleep and care rhythm, the arrangement comprising:
one or more baby sensors, comprising at least one of a motion sensor and a microphone, positioned and programmed to continuously measure data from the baby;
one or more mother sensors, comprising at least one of a motion sensor and a microphone, positioned and programmed to continuously measure data from the mother or another caregiver;
two or more actuators comprising an electromechanical transducer and an airflow blower, positioned to give audio, motion and airflow actions to the baby; and
an artificial intelligence unit, which has been configured and coded to receive data from the one or more baby sensors and the one or more mother sensors, analyze and process the data received from the one or more baby sensors with algorithms saved in a baby behaviour database and a control unit in real-time to produce and save the baby's sleep/activity status graph, and analyze and process the data received from the one or more mother sensors with saved algorithms in real-time to produce and save the mother's sleep/emotion status graph; and
select from an audio/motion/airflow database a data file comprising an optimal combination of the audio, motion and airflow actions to control the two or more actuators to calm and soothe the baby, which selection is based on a history of previous selections saved in the baby behavior database and an analysis of how different previous selections of the audio, motions and airflow actions changed a sleep/activity status of the baby as presented in the baby's sleep/activity status graph and a sleep/emotion status of the mother presented in the mother's sleep/emotion status graph as determined by finding interactivity and dependability between the baby's sleep/activity status graph and the mother's sleep/emotion status graph presently and in their histories and define the best way to treat the baby according to historic experiments of baby behaviour changes according to previously used combinations of the audio, motion and airflow actions.

2. The baby care arrangement of claim 1, wherein the one or more baby sensors are any combination of
sensors fixed on a platform under a mattress of a baby nest, comprising movement sensors, microphones, and temperature, humidity and chemical sensors, which are used to measure and track any combination of the baby's presence, motions, voice, heart rate, breathing rate, sounds from lung and respiratory track, temperature changes, baby's crying, joggling, talking, breathing, urinating, excreting, farting, burping and silence;
sensors fixed on a sensor sheet under the baby laying on a baby care device, comprising Electroencephalography (ECG), Electroencephalogram (EEG), Electromyography (EMG), Skin Dermal Activity (SDA), temperature, humidity, infrared, Near Infrared Spectroscopy (NIRS), oxygen saturation, chemical and movement sensors and microphones, which are used to measure and track any combination of ECG, EEG, EMG, SDA, oxygen saturation, skin conductivity, skin temperature, humidity, urinating, excreting, farting, silence,
and the one or more mother sensors are any combination of sensors, comprising heart sensors, microphones, movement sensors and bioelectric sensors, which are used to measure and track any combination of the following: the mother's or the another caregiver's body and arm movements, body temperature comprising fever and daily variations of body temperature, heart activities comprising pulse and ECG, lung activities comprising breathing rate and airflow curve, pauses, blood circulation comprising oxygen saturation, flow volume, blocks, body temperature distribution, brain activities comprising EEG, oxygen saturation, muscle activities comprising EMG, skin activities comprising conductance, sweating, gastro/metabolic activities, speaking, humming, singing, breathing, sighing, environmental sounds coming from home life, other children, kitchen machinery and outdoor traffic;
wherein while a minimum combination of the sensors are one movement sensor and one microphone on the platform and one movement sensor and one microphone on the mother or the another caregiver.

3. The baby care arrangement of claim 2, wherein the sensor data for the artificial intelligence unit is also collected using room sensors, which are positioned and programmed to continuously measure environmental conditions in a baby caring room or place, and comprising any combination of microphones and sensors for light, temperature, humidity and other smart home parameters, which are used to measure and track any combination of the following: presence of anybody in the room, temperature, light, humidity, air pollution, distinct sound, noise and radiation.

4. The baby care arrangement of claim 3, wherein the artificial intelligence unit has been further configured and coded:
to determine the interactivity and dependability between the baby's sleep/activity status graph and the mother's sleep/emotion status graph presently and in their histories and define the best way to treat the baby according to historic experiments of baby behaviour changes according to previously used combinations of the audio, motion and airflow actions;
to control the audio, motion and airflow actions in the selected optimal way, to help the baby find an optimal sleep/activity level, which belongs to an existing instance and existing conditions, comprising a phase of the baby's awake and sleep rhythm, the mother's or the another caregiver's emotional status and a time period history, and the environmental conditions in the baby caring room or place, and the time period history; and to store data of used audio, motion and airflow actions combined with the data of the baby's sleep/activity status graph and the mother's sleep/emotion status graph and environmental data and the time period history into the baby behavior database in a manner that all collected baby behavior data from a short term time period comprising one or more of minutes and hours and a long term time period comprising one or more of days, months and years of tracking history are available, based upon which the artificial intelligence unity makes decisions for future actions.

5. The baby care arrangement of claim 1, wherein the audio, motion and airflow actions for a certain emotional status of the mother or the another caregiver are determined and realized by:
recording, in the audio/motion/airflow database, at least two emotional statuses comprising joyful and peaceful states of the mother or the another caregiver, intrauterine acoustical and physical vibrations and motions of the mother or the another caregiver comprising vibrations originating from heart activities and blood flow, lung activities and air flow, intestine fluctuations and vocal cord activities; and
formulating the data file of the audio, motion and airflow actions to produce similar sounds; and
movements from a surface of the platform, in a manner that simulates artificially an acoustical and physical environment of the baby while in uterine or in a lap of the mother or the another caregiver, and produces an airflow from an airflow pipe that simulates artificial breathing of the mother or the another caregiver while having the baby in the lap of the mother or the another caregiver; and
storing the formulated data file of the audio, motion and airflow actions-files with labelling data of a respective emotional status of the mother or the another caregiver into the audio/motion/airflow database.

6. The baby care arrangement of according to claim 5, wherein the audio, motion and airflow actions are synchronized on the mother's or the another caregiver's real-time heart rate and breathing rate, which control pulsations of heart and breathing originated sounds and vibrations respectively.

7. The baby care arrangement of claim 4, wherein the audio, motion and airflow action data files are determined and realized artificially from recordings of the mother or the another caregiver speaking, lulling, humming or singing in at least two different emotional statuses comprising joyful and peaceful states and during different baby caring actions comprising bottle feeding, breast feeding, medication giving, dressing, undressing, nappy changing, caressing by touching, playing with the baby or other daily baby caring events, and by storing the audio, motion and airflow action data files with the labelling data of the respective emotional statuses of the mother or the another caregiver, and baby caring events.

8. The baby care arrangement of claim 1, wherein the daily sleeping and eating rhythms of the baby are stored together with labelling data of used manual baby caring actions and used audio, motion and airflow actions in the baby behavior database used by the artificial intelligence unit in decision making of the actions to be used in phases of the sleeping and eating rhythms of the baby.

9. The baby care arrangement of claim 1, wherein the baby's sleep/activity status is communicated back to the mother or the another caregiver while physically distant from the baby and execution of care actions from the data file of the audio/motion/airflow database is done from far distance by using a mobile phone or a smart watch application.

10. The baby care arrangement of claim 1, wherein the baby care arrangement comprises means to recognize and stop Sudden Infant Death Syndrome seizure by tracking breathing of the baby with a Sudden Infant Death Syndrome detection algorithm, which first detects a pause in breathing for longer than a preset time period ranging from 30 to 120 seconds and then starts an audio, motion and airflow action with a preset loud, noisy sound and strong shaking contents and, based on the baby not starting breathing again within a next 30-60 seconds, the means to recognize and stop Sudden Infant Death Syndrome seizure sends a preset Sudden Infant Death Syndrome alarm to one or more of the mother or the another caregiver.

11. The baby care arrangement of claim 1, wherein the baby care arrangement comprises;
means to track a temperature of the baby with temperature sensors on one or more of the platform or a sensor sheet;
means to heat and cool the platform; and
means to add heating and cooling actions to the data file of the audio, motion and airflow actions.

12. The baby care arrangement of claim 1, wherein the baby care arrangement comprises means to enhance an effect of the audio, motion and airflow actions by one or more of simultaneous swinging and tightening of the baby nest around the baby to simulate a feeling of being in arms of the mother or another caregiver.

13. The baby care arrangement of claim 1, wherein the baby care arrangement comprises
means to recognize the baby is sleeping too long due to becoming sick or having travelled and been awaken for a long period, even several hours, or for any other reason, which has confused a sleeping rhythm of the baby; and
means to wake the baby up, based on the baby sleeping too long, for feeding, nap-changing or playing with by switching on a familiar song or recorded speaking or humming of the mother or the another caregiver from an electromechanical transducer.

14. The baby care arrangement of claim 1, wherein a vibrating platform comprises two parallel plates, which are formed by an upper plate and a lower plate, and the upper plate of the vibrating platform is made of a rigid material, which carries vibrations on a surface to radiate to the baby smoothly from a wide area.

15. The baby care arrangement of according to claim 14, wherein a size of the vibrating platform is a size of a mattress for the baby and a thickness is 10-30 millimeters (mm), while a thickness of the two parallel plates is less than 5 mm, and the rigid material of the upper plate is plywood with a density of 600-700 kilograms per cubic meter ($kg/m^3$) with thickness of 3-5 mm and a modulus of bending elasticity along fibers of surface layers of the plywood is between 12 and 17 kilonewtons per square millimeter ($kN/mm^2$).

16. A baby care method for helping a mother or another caregiver with a baby to find optimal life, sleep and care rhythm, the method comprising:
  by-multi-modally measuring and tracking:
    via one or more baby sensors, one or more of the baby's presence, motions, voice, heart rate, breathing rate, sounds from lung and respiratory track, and temperature changes, and baby's crying, joggling, talking, breathing, urinating, excreting, farting, burping and silence; and
    one or more of the baby's Electroencephalography (ECG), Electroencephalogram (EEG), Electromyography (EMG), Skin Dermal Activity (SDA), skin conductivity, skin temperature, humidity, and brain activity; and
    via one or more mother sensors, one or more of the mother's or the another caregiver's body and arms movements, body temperature, heart activities, lung activities, blood circulation, brain activities, muscle activities, skin activities and gastro/metabolic activities; and
    one or more of the mother's or another caregiver's speaking, humming, singing, breathing, sighing, and environmental sounds coming from one or more of a home life, other children, kitchen machinery and outdoor traffic; and
    via environmental sensors, one or more environmental conditions in a care room comprising at least one of a presence of anybody in the care room, temperature, light, humidity, air pollution, distinct sound, noise and radiation; or
    the measuring and tracking further, comprising at least baby's movements and voices and the mother's or another caregiver's movements and voices;
  wherein a sleep/activity status graph of the baby and a sleep/emotion status graph of the mother or another caregiver are processed from the measuring and tracking, in an artificial intelligence system via one or more processors of a data processing device;
    to find interactivity and dependability between a sleep/activity graph of the baby and a sleep/emotion status graph of the mother now and in their histories and to define an optimal way to treat the baby according to historic experiments of baby behaviour changes according to used different audio, motion and airflow actions; and
    to control audio, motion and airflow actions in a defined optimal way, to help the baby to find an optimal sleep or activity level, which belongs to existing instance and existing conditions, comprising a phase of an awake or sleep rhythm of the baby, the mother's or another caregiver's emotional status and time period histories, the one or more environmental conditions in the care room, and time period history; and
  to store data of used audio, motion and airflow actions combined with data of the sleep/activity status graph of the baby and the sleep/emotion status graph of the mother and environmental data and the time period history into a baby behavior database in a manner that all collected baby behavior data from a short term time period comprising one or more of minutes and hours and a long term time period comprising one or more of days, months and years of tracking history are available, based upon which an artificial intelligence system makes decisions for future actions.

17. The baby care method of claim 16, wherein also a spouse is provided with one or more mother sensors and a sleep or emotion graph of the spouse is tracked and utilized in optimizing baby care by alarming the spouse to care for the baby,
  based on the baby waking up too early and it is not yet time to breast-feed the baby and the trials to change the audio, motion and airflow actions does not help to get the baby back to sleep; or
  the sleep/emotion status graph of the mother and the sleep/emotion status graphs of the spouse shows that the spouse is sleeping lighter and has been sleeping longer than the mother; or
  any other intelligent comparison shows that it is optimal for a whole family to alarm the spouse instead of the mother.

18. The baby care method of claim 16, wherein manual baby care actions are automatically detected and tracked by sensors in a manner that room sensors track a presence of the mother in the care room, platform acceleration sensors sense laying down of the baby on a platform, platform microphones sense sounds coming from the baby sucking a feeding bottle, mother acceleration sensors sense breast-feeding of the baby and mother microphones and arm movement sensors are configured to hear and detect a burping action of the baby.

19. A non-transitory computer readable medium for improving emotional interaction between a mother or another caregiver and a baby and a baby's life and sleep rhythm, the non-transitory computer readable medium comprising instructions, which when executed by one or more processors of a data processing device, cause the one or more processors to:
  record and aggregate sensor data from sensors on a platform and sensors on a sensor sheet, and processing a sleep/activity status graph in a baby signal conditioning and data aggregation artificial intelligence system; and
  record and aggregate sensor data from sensors on the mother or another caregiver and processing a sleep/emotion status graph in a mother signal conditioning and data aggregation artificial intelligence system; and
  record and aggregate sensor data from sensors in a care room; and processing environmental status data in a smart home environmental signal conditioning and data aggregation artificial intelligence system; and
  generate audio, motion and airflow action files by inputting recorded sensor data, using given artificial intelligence algorithms and storing the audio, motion and airflow action files in an audio/motion/airflow database; and
  record baby behaviour files comprising life and sleep rhythm data with specification data of used manual and automatic care actions, and storing the baby behaviour files in a baby behaviour database; and
  generate alarms and reports to a mobile alarm unit; and
  realize a gateway between a baby care arrangement and a smart home system; and
  realize a gateway between the baby care arrangement and any social media,
wherein for optimization of an effect of audio, motion and airflow actions, the non-transitory computer readable medium further comprising instructions, which when executed by the one or more processors of the data processing device, further cause the one or more processors to:
  analyze in an artificial intelligence unit the sleep/activity status graph and the sleep/emotion status graph, their first and second time derivatives, found rhythms and similarities, and correlations between the sleep/activity status graph and the sleep/emotion status graph, correlations between the first and second time derivatives of the sleep/activity status graph and the sleep/emotion status graph, and tracked data from environmental room sensors and events in them, which are used as features in data mining for finding best audio, motion, and airflow actions to help the baby to move from one sleep or activity level to another or to calm down to fall asleep; and realize an automatic tracking process to read a sleep/activity level data and analyse whether the sleep/activity level data has changed to a right way and to execute a decision making task to change an audio/motion/airflow action data file to a better working one from the audio/motion/airflow database; and alarm the mother or the another caregiver based on a sleep/activity status of the baby being in a panic level; and follow up on whether the baby continues sleeping or is waking up; and based on the baby waking up, for checking whether it is the right time to wake up, and if not, to return back to try to get the baby fall asleep again; or softly waking the baby up based on the baby sleeping too long.

20. The non-transitory computer readable medium according to claim 19, wherein for optimization of selection and adjusting the audio, motion and airflow actions, the non-transitory computer readable medium further comprises instructions, which when executed by the one or more processors of the data processing device, further cause the one or more processors to:

exchange the audio/motion/airflow action data files with other users in one or more social media communities; and utilize experiments of other users to find a best choice of the audio/motion/airflow action data files and their further adjustments according to the sensor data from the sensors on the platform or the sensors on the sensor sheet.

\* \* \* \* \*